(12) United States Patent
Yoshino et al.

(10) Patent No.: US 7,837,329 B2
(45) Date of Patent: Nov. 23, 2010

(54) FUNDUS CAMERA

(75) Inventors: Masayuki Yoshino, Gamagori (JP);
Yoshiaki Mimura, Gamagori (JP);
Akira Tawada, Gamagori (JP); Naoki Ichikawa, Okazaki (JP)

(73) Assignee: Nidek Co., Ltd., Aichi-ken (JP)

( * ) Notice: Subject to any disclaimer, the term of this patent is extended or adjusted under 35 U.S.C. 154(b) by 0 days.

(21) Appl. No.: 12/415,547

(22) Filed: Mar. 31, 2009

(65) Prior Publication Data
US 2009/0244483 A1 Oct. 1, 2009

(30) Foreign Application Priority Data
Mar. 31, 2008 (JP) ............................ 2008-092397
Sep. 30, 2008 (JP) ............................ 2008-255757
Feb. 24, 2009 (JP) ............................ 2009-040245

(51) Int. Cl.
*A61B 3/14* (2006.01)
(52) U.S. Cl. ......................... 351/206; 351/212; 351/221
(58) Field of Classification Search ................. 351/206, 351/221, 207, 208, 209, 210, 211, 212, 213, 351/214, 215, 246
See application file for complete search history.

(56) References Cited

U.S. PATENT DOCUMENTS 7,219,996 B2 * 5/2007 Ichikawa ................... 351/206

2007/0030451 A1 * 2/2007 Ishihara et al. ............. 351/206

FOREIGN PATENT DOCUMENTS

| EP | 1752084 A2 | 2/2007 |
| JP | 2007151651 A | 6/2007 |
| JP | 2007-202724 | 8/2007 |

* cited by examiner

*Primary Examiner*—Hung X Dang
(74) *Attorney, Agent, or Firm*—Muncy, Geissler, Olds & Lowe, PLLC

(57) ABSTRACT

A fundus camera favorably performing focusing on a fundus of an examinee's eye without a black dot plate in a target projection optical system comprises an illumination optical system comprising a light source and an objective lens, a photographing optical system comprising a focusing lens movable in the optical axis direction and a diopter correction lens to correct a diopter of severe ametropia, a first moving mechanism comprising a first driving unit moving the focusing lens, a focus detection optical system comprising a projection optical system comprising a light source and a photo-receiving optical system comprising a photodetector, a second moving mechanism comprising a second driving unit moving a part of the detection optical system including at least one of the projection light source and the photodetector in the optical axis direction, a monitor, and a control unit controlling the second unit in conjunction with movement of the focusing lens.

4 Claims, 7 Drawing Sheets

FUNDUS CAMERA

BACKGROUND OF THE INVENTION

1. Field of the Invention

The present invention relates to a fundus camera which photographs a fundus of an examinee's eye.

2. Description of Related Art

Conventionally, a fundus camera which photographs a fundus of an examinee's eye comprises a focusing lens which is movable in an optical axis direction and is placed in a photographing optical path of a photographing optical system in order to perform focusing on the fundus. In addition, the fundus camera comprises an optical system for projecting light of split targets onto the fundus via a spot mirror attached to a focus lever which is inserted into and removed from an optical path of a fundus illumination optical system, and photo-receiving the light of the split targets reflected from the fundus by an image pickup element of a fundus observation optical system. An examiner grasps a focus deviation based on a separation state between images of the split targets (focus targets) when an image picked up by the image pickup element of the fundus observation optical system is displayed on a monitor.

As a prior art literature relating to the present invention, Japanese Patent Application Unexamined Publication No. 2007-202724 is cited.

In the case of projecting the focus targets as described above, a black dot plate is provided in the focus target projection optical system in order to remove reflection light from an objective lens which results from the light of the split targets. In such a case, there is a first problem that the degree of freedom of optical engineering is limited. For example, a moving range of the focus lever is limited by providing the black dot plate in the focus target projection optical system. Accordingly, when a diopter correction lens is inserted, the focus targets cannot be favorably photographed, and focus adjustment is visually performed with the focus lever being removed from the optical path and the focus targets being not presented.

In recent years, an image of the fundus is often picked up by a high-resolution two-dimensional image pickup element, and the obtained fundus image is displayed and observed on a large screen of a display of a personal computer. This brings about a second problem that when a fundus of an eye with severe myopic is photographed, an image of the fundus is blurred even though the photographing is performed with the fundus in focus, and accordingly observation could be difficult to perform.

It is difficult for a photographer to judge the cause of the blurred fundus image and take measures against the blurred fundus image.

SUMMARY OF THE INVENTION

An object of the invention is to overcome the first problem described above and to provide a fundus camera capable of favorably performing focusing on a fundus of an examinee's eye without being provided with a black dot plate in an optical system for projecting focus targets. Another object of the invention is to overcome the second problem described above and to provide a fundus camera by which a state of an examinee's eye is easily known during photographing.

To achieve the objects and in accordance with the purpose of the present invention, a fundus camera comprises an illumination optical system comprising an illumination light source, for illuminating the fundus with illumination light emitted from the illumination light source via an objective lens, a photographing optical system comprising a focusing lens movable in an optical axis direction thereof, for photographing the fundus by photo-receiving the illumination light reflected from the fundus via the objective lens and the focusing lens, wherein a diopter correction lens arranged to correct a diopter of severe ametropia is placed to be insertable into and removable from an optical path of the photographing optical system, a first moving mechanism comprising a first driving unit, which is arranged to move the focusing lens in the optical axis direction, a focus detection optical system comprising a projection optical system comprising a projection light source, for projecting focus target light onto the fundus, and a photo-receiving optical system comprising a photodetector, for photo-receiving the focus target light reflected from the fundus, and a second moving mechanism comprising a second driving unit, which is arranged to move a part of the focus detection optical system in an optical axis direction thereof, wherein the part of the focus detection optical system includes at least one of the projection light source and the photodetector, and the second moving mechanism has a movable range including a diopter range which is corrected when the diopter correction lens is inserted, a monitor, and a control unit arranged to control driving of the second driving unit in conjunction with movement of the focusing lens, wherein when the diopter correction lens is inserted, the part of the focus detection optical system is moved to a position corresponding to a diopter which is corrected by the diopter correction lens and the focusing lens.

In another aspect of the present invention, a fundus camera comprises a fundus photographing optical system comprising a focusing lens movable in an optical axis direction thereof, for photographing the fundus, an eye refractive power measurement data obtaining unit arranged to obtain measurement data including astigmatic power of the eye, a first focus detection unit arranged to detect a focusing state of the fundus camera with respect to the fundus, a monitor, and a control unit arranged to control the monitor to display, as first focusing information, the focusing state detected by the first focus detection unit, wherein the control unit is arranged, when the focusing lens is moved by using the obtained measurement data, to set a focusing completion position of the focusing lens at a position corresponding to spherical equivalent power of the eye, and control the monitor to change to display focusing information based on the set position as second focusing information which is different from the first focusing information.

Yet, in another aspect of the present invention, a fundus camera further comprises a photographing optical system comprising a focusing lens movable in an optical axis direction thereof and a first image pickup element, for photographing the fundus, an observation optical system comprising a second image pickup element, for observing the fundus, a corneal target projection optical system for projecting a target for corneal astigmatism detection onto a cornea of the eye, a target detection optical system comprising a two-dimensional photodetector, for detecting the target projected onto the cornea, a monitor, and a control unit arranged to process an output signal from one of the first image pickup element and the second image pickup element and control the monitor to display one of a photographing image of the fundus and an observation image of the fundus, wherein the control unit is arranged to determine whether or not corneal astigmatism is present in the eye based on an image forming position of the target on the photodetector and control the monitor to display a result of the determination together with one of the fundus photographing image and the fundus observation image.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
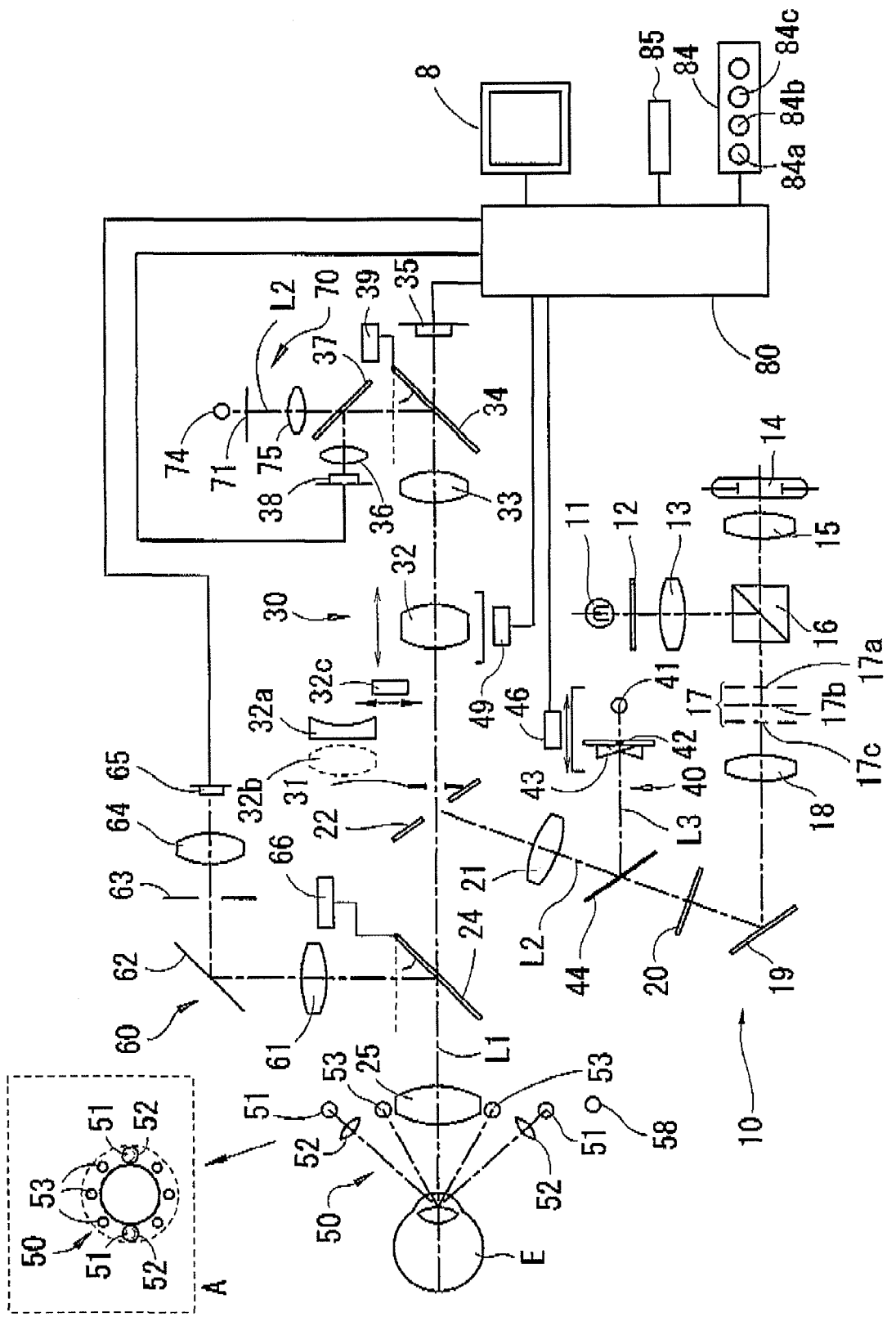
FIG. 1 is a schematic view showing an optical system and a control system of a fundus camera according to a first preferred embodiment of the present invention.

A detailed description of preferred embodiments of a fundus camera embodied by the present invention is provided below with reference to the accompanying drawings. FIG. 1 is a schematic view showing an optical system and a control system of a fundus camera according to a first preferred embodiment of the present invention. The optical system comprises an illumination optical system 10, a fundus observation/photographing optical system 30, a focus target projection optical system 40, an alignment target projection optical system 50, an anterior-segment observation optical system 60, and a fixation target presenting optical system 70.

Illumination Optical System 10

The illumination optical system 10 comprises an observation illumination optical system and a photographing illumination optical system. The photographing illumination optical system comprises a photographing light source 14 such as a flash lamp, a condenser lens 15, a first shielding plate 17a having a circular shielding portion (e.g., a ring slit), a ring slit 17b having a circular shielding portion at the center and a ring-shaped opening, a second shielding plate 17c having a circular shielding portion (e.g., a ring slit), a relay lens 18, a total reflection mirror 19, a black dot plate 20 having a black dot at the center, a relay lens 21, an apertured mirror 22, and an objective lens 25.

The observation illumination optical system comprises a light source 11 such as a halogen lamp, an infrared transmission filter 12 which transmits near infrared light having a wavelength of 750 nm or more, a condenser lens 13, a dichroic mirror 16 placed between the condenser lens 13 and the ring slit 17b, and the first shielding plate 17a through the objective lens 25. The dichroic mirror 16 has properties of reflecting light from the light source 11 and transmitting light from the photographing light source 14.

In the optical systems, when an examinee's eye E and an apparatus main body (not shown) have a positional relation such that the apparatus main body is placed at a predetermined alignment reference position (reference center) with respect to the eye E, the ring slit 17b is placed at a position conjugate with a pupil (an iris) of the eye E, the first shielding plate 17a is placed at a position conjugate with a cornea of the eye E, and the second shielding plate 17c is placed at a position conjugate with a posterior surface of a crystalline lens of the eye E. The first shielding plate 17a, the ring slit 17b, and the second shielding plate 17c in the illumination optical system 10 constitute a shielding member 17. The shielding member 17 functions as flare removing means for preventing corneal reflection light and crystalline lens reflection light formed by fundus photographing light from being included in fundus reflection light and photo-received on a two-dimensional, image pickup element 35 for photographing to be described later.

Fundus Observation/Photographing Optical System 30

The fundus observation/photographing optical system 30 for photographing an image of a fundus of the eye E comprises a fundus observation optical system and a photographing optical system. The fundus observation/photographing optical system 30 comprises the objective lens 25, a photographing diaphragm 31 placed in the vicinity of an aperture of the apertured mirror 22, a focusing lens 32 movable in the direction of a photographing optical axis L1, an image forming lens 33, and a pop-up mirror 34 which is insertable into and removable from an optical path by means of an inserting/removing mechanism 39. The photographing optical system and the fundus observation optical system share the objective lens 25, and the photographing diaphragm 31 through the image forming lens 33. The photographing diaphragm 31 is placed at a position substantially conjugate with the pupil with reference to the objective lens 25. The focusing lens 32 is moved in the direction of the optical axis L1 by means of a moving mechanism 49 having a motor. The image pickup element 35 has sensitivity to a visible wavelength range. On an optical path in a reflecting direction of the pop-up mirror 34, a polarization beam splitter 37 reflecting p-polarized light and transmitting s-polarized light, a relay lens 36, and a two-dimensional image pickup element 38 for observation having sensitivity to an infrared wavelength range are placed. Provided between the focusing lens 32 and the photographing diaphragm 31 are diopter correction lenses 32a and 32b (i.e., a negative power lens 32a and a positive power lens 32b) which are insertable into and removable from the photographing optical path of the fundus observation/photographing optical system 30 by driving of a driving unit 32c. If the eye E has severe ametropia, the diopter correction lens 32a or 32b is inserted into the optical path manually or automatically. When the diopter correction lens 32a or 32b is inserted into the optical path, a diopter correction amount corresponding to the inserted diopter correction lens is added to the fundus observation/photographing optical system 30.

A dichroic mirror (a wavelength selecting mirror) 24 which functions as an optical path dividing member is placed obliquely on an optical path between the objective lens 25 and the apertured mirror 22 and is insertable into and removable from the optical path. The dichroic mirror 24 has properties of reflecting light within an infrared wavelength range of approximately 900 nm or more including light from the alignment target projection optical system 50 and light from an anterior-segment illumination light source 58, and transmitting light within an infrared wavelength range of approximately 900 nm or less including light from the light source 11. At the time of fundus photographing, the dichroic mirror 24 is flipped up by an inserting/removing mechanism 66 and removed from the optical path. A known mechanism such as a solenoid and a cam may be used for the inserting/removing mechanism 66.

Light emitted from the light source 11 is made into infrared light by the infrared filter 12, passes through the condenser lens 13, and is reflected by the dichroic mirror 16 so as to illuminate the first shielding plate 17a. The light transmitted through the first shielding plate 17a passes through the ring slit 17b, the second shielding plate 17c, the relay lens 18, the mirror 19, the black point plate 20, and the relay lens 21 to reach the apertured mirror 22. The light reflected from the apertured mirror 22 is transmitted through the dichroic mirror 24, is made to converge once in the vicinity of the pupil by the objective lens 25, and then diffuses to illuminate the fundus.

The light reflected from the fundus passes through the objective lens 25, the dichroic mirror 24, the aperture of the apertured mirror 22, the photographing diaphragm 31, the focusing lens 32, the image forming lens 33, the pop-up mirror 34, the polarization beam splitter 37, and the relay lens 36 to form an observation image of the fundus on the image pickup element 38. Output of the image pickup element 38 is inputted to a control unit 80, and the fundus observation image picked up by the image pickup element 38 is displayed on a monitor 8.

Visible light emitted from the photographing light source 14 passes through the condenser lens 15 and the dichroic mirror 16, and goes along the same optical path as the illumination light for fundus observation, so that the fundus is illuminated by the visible light. The light reflected from the fundus passes through the objective lens 25, the aperture of the apertured mirror 22, the photographing diaphragm 31, the focusing lens 32, and the image forming lens 33 to form a photographing image of the fundus on the image pickup element 35. Focus target projection optical system 40

The focus target projection optical system 40 comprises an infrared light source 41, a slit target plate 42, two deflection-angle prisms 43 attached to the slit target plate 42, and a polarization beam splitter 44. The projection optical system 40 shares an optical path from the polarization beam splitter 44 through the objective lens 25 with the illumination optical system 10. The polarization beam splitter 44 is placed in an optical path of the illumination optical system 10 and is used as an optical coupler (a beam combiner) arranged to couple the optical path of the illumination optical system 10 and an optical path of the projection optical system 40.

In the projection optical system 40, the deflection-angle prisms 43 which are arranged to make light deflected in vertically-corresponding directions are aligned laterally interposing a projection optical axis L3 and coincide with a slit which is laterally provided in the target plate 42.

The projection optical system 40 comprises a first polarizing member arranged to make focus target light have a predetermined polarization direction. The observation optical system 30 comprises a second polarizing member arranged to limit, for the image pickup element 38, the focus target light having the predetermined polarization direction of the first polarizing member.

For example, the projection optical system 40 and the observation optical system 30 comprise linearly polarizing plates having polarizing directions intersecting at right angles, or polarization beam splitters having properties of transmitting or reflecting one light in order to making the light head for the eye E and reflecting or transmitting the other light in order to make the light photo-received on the image pickup element 38, the light having polarizing directions intersecting at right angles. Accordingly, the focus target light reflected by the objective lens 25 is prevented from heading for the image pickup element 38.

To be specific, the polarization beam splitter 44 is placed between the light sources of the illumination optical system 10 (i.e., the light source 11 and the light source 14) and the apertured mirror 22 (including a case when the polarization beam splitter 44 is insertable and removable). For the polarization beam splitter 44, a polarization beam splitter transmitting p-polarized light and reflecting s-polarized light is preferably used. The optical axis L3 of the projection optical system 40 may be placed at a position deviated in a vertical direction with respect to an optical axis L2 of the illumination optical system 10 in order to prevent focus targets on the fundus from coinciding with a shadow of the black dot plate 20.

The projection light emitted from the light source 41 passes through the slit of the target plate 42, is subjected to angle deflection into the respective directions by the deflection-angle prisms 43, and is reflected by the polarization beam splitter 44. In the light emitted from the light source 41 (natural light), s-polarized light is reflected by the polarization beam splitter 44.

The light reflected by the polarization beam splitter 44 (the s-polarized light) passes through the relay lens 21, the apertured mirror 22, the dichroic mirror 24, and the objective lens 25, and is projected onto the fundus. The focus light projected onto the fundus is made into p-polarized light and s-polarized light by being subjected to diffuse deflection by the fundus. The light reflected from the fundus passes through the objective lens 25 and the aperture of the apertured mirror 22 through the pop-up mirror 34 to enter the polarization beam splitter 37. In the fundus reflection light, the p-polarized light is reflected by the polarization beam splitter 37 and the s-polarized light is transmitted by the polarization beam splitter 37. An image of the fundus reflection light reflected by the polarization beam splitter 37 (the p-polarized light) is picked up by the image pickup element 38 via the relay lens 36.

In the above case, the projection optical system 40 is used as a target projection optical system which has a projection light source and projects focus targets onto the fundus. The observation optical system 30 comprising the image pickup element 38 is used as a photo-receiving optical system comprising a photodetector for photo-receiving the fundus reflection light from the projection optical system 40. Accordingly, the projection optical system 40 and the observation optical system 30 constitute a focus detection optical system.

Figure 2A:
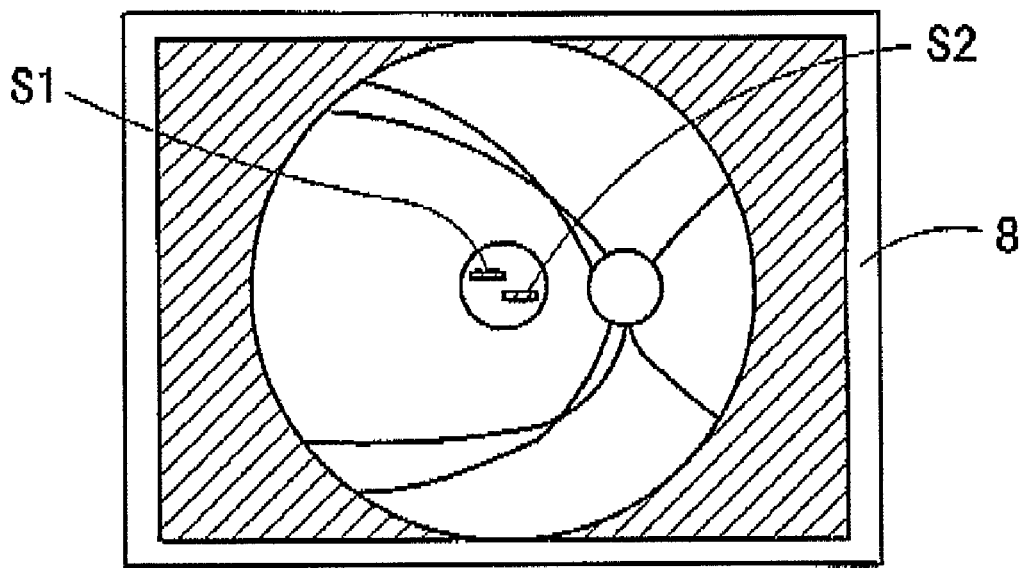
FIGS. 2A and 2B are views showing focus target images projected onto a fundus of an examinee's eye.
Figure 2B:
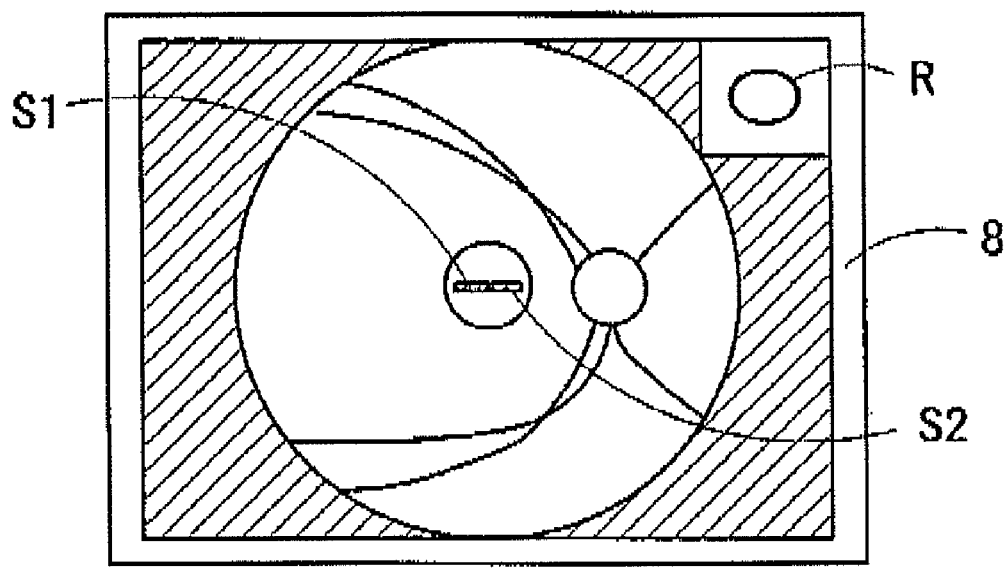

FIGS. 2A and 2B are views showing the monitor 8 on which images outputted from the image pickup element 38 are displayed. As shown in FIGS. 2A and 2B, when split targets (focus targets) are projected onto the fundus, focus target images S1 and S2 are formed. The focus target images S1 and S2 are separate in a given direction on the fundus in accordance with a focusing state of the apparatus with respect to the fundus. The focus target images S1 and S2 are picked up by the image pickup element 38 together with the fundus image.

When an image-pickup signal from the image pickup element 38 is outputted to the monitor 8, an examiner is allowed to grasp a focus deviation based on a state separation between the focus target images S1 and S2. The control unit 80 electrically detects the focusing state of the apparatus with respect to the fundus based on the separation state between the focus target images S1 and S2 and automatically moves the focusing lens 32 based on a result of the detection (automatic focusing control).

The focus target light is subjected to substantial specular reflection when passing through lens surfaces of the objective lens 25, the cornea, and the crystalline lens, and accordingly reaches the polarization beam splitter 37 in the state of the s-polarized light. Thus, it is possible to prevent flare and ghost caused by the projection of the focus targets from entering the image pickup element 38.

A part of the projection optical system 40 including the light source 41 (i.e., the light source 41, the slit target plate 42, and the deflection-angle prisms 43) is moved in the optical axis direction in conjunction with the movement of the focusing lens 32. For example, when the focusing lens 32 is located in a position for an emmetropic eye, the part of the projection optical system 40 including the light source 41 is moved so that the fundus of the emmetropic eye and the slit of the slit target plate 42 are substantially conjugate. When the focusing lens 32 is located in a position such that an eye with given sphere power (e.g., −3 D) is in focus, the part of the projection optical system 40 including the light source 41 is moved so that the fundus of the eye and the slit of the target plate 42 are substantially conjugate.

A moving mechanism 46 comprises a motor and moves the part of the projection optical system 40 including the light source 41 in the optical axis direction with respect to the polarization beam splitter 44. A movable range of the part of the projection optical system 40 covers a movable range corresponding to a diopter correction amount which is obtained only by the movement of the focusing lens 32 and a movable range corresponding to a diopter correction amount which is obtained by the insertion of the diopter correction lens 32*a* or 32*b*. In other words, the moving mechanism 46 has a movable range including a diopter correction range which is obtained by the movement of the focusing lens 32 with the diopter correction lens being inserted.

In this case, the movable range of the part of the projection optical system 40 is changed in accordance with the insertion/removal state of the diopter correction lenses 32*a* and 32*b* in the photographing optical path. When the movable range is set in accordance with the insertion/removal state of the diopter correction lenses 32*a* and 32*b*, the part of the projection optical system 40 is moved within the movable range in conjunction with the movement of the focusing lens 32 (detailed descriptions are provided later).

Alignment Target Projection Optical System 50

As shown in the dashed lined box A at the upper left of FIG. 1, the alignment target projection optical system 50 for projecting alignment target light is configured such that a plurality of infrared light sources are concentrically arranged at intervals of 45 degrees having the optical axis L1 at the center. To be specific, the alignment target projection optical system 50 comprises first target projection optical systems having infrared light sources 51 and collimating lenses 52 and arranged laterally symmetrical with respect to the optical axis L1 (0 degree and 180 degrees), and second target projection optical systems having six infrared light sources 53 and arranged at positions different from those of the first target projection optical systems. The first projection optical systems project infinite targets onto the cornea from right and left directions, and the second projection optical systems project finite targets onto the cornea from up and down directions or oblique directions. In the main drawing of FIG. 1, the first target projection optical systems (0 degree and 180 degrees) and a part of the second target projection optical systems (45 degrees and 135 degrees) are shown for the sake of illustration.

Anterior-Segment Observation Optical System 60

The anterior-segment observation (photographing) optical system 60 for picking up an observation image of an anterior-segment of the eye E comprises a field lens 61, a total reflection mirror 62, a diaphragm 63, a relay lens 64, and a two-dimensional image pickup element (photodetector) 65 having sensitivity to the infrared wavelength range, which are arranged in a reflecting direction of the dichroic mirror 24. The image pickup element 65 doubles as image pickup means for alignment target detection, and picks up the image of the anterior-segment illuminated by the illumination light source 58 and an image of an alignment target. Illumination light emitted from the illumination light source 58 is reflected by the anterior-segment, and the light reflected from the anterior-segment passes through the objective lens 25, the dichroic mirror 24, and the field lens 61 through the relay lens 64, and is photo-received on the image pickup element 65. Alignment target light emitted from the light sources of the alignment target projection optical system 50 is projected onto the cornea, and the light reflected from the cornea is photo-received on (projected onto) the image pickup element 65 via the objective lens 25 through the relay lens 64. Output of the image pick up element 65 is inputted to the control unit 80, and the anterior-segment image picked up by the image pickup element 65 is displayed on the monitor 8. The anterior-segment observation optical system 60 doubles as means for detecting an alignment state of the apparatus main body with respect to the eye E.

Fixation Target Presenting Optical System 70

The fixation target presenting optical system 70 for presenting a fixation target for fixation of the eye E comprises a red light source (a fixation lamp) 74, a shielding plate 71 with an opening, and a relay lens 75. The fixation target presenting optical system 70 shares an optical path from the pop-up mirror 34 through the objective lens 25 with the fundus observation/photographing optical system 30 via the polarization beam splitter 37.

The fixation target is formed by illuminating the shielding plate 71 from behind by the light source 74. Illumination light emitted from the light source 74 passes through the opening of the shielding plate 71, the relay lens 75, the polarization beam splitter 37, the pop-up mirror 34, the image forming lens 33, the focusing lens 32, the apertured mirror 22, the dichroic mirror 24, and the objective lens 25, and converges at the fundus, so that the examinee visually perceives the light from the opening of the shielding plate 71 as the fixation target.

Control System

The image pickup elements 65, 38 and 35 are connected to the control unit 80. The control unit 80 detects the alignment target in the anterior-segment image picked up by the image pickup element 65. The control unit 80 detects and processes the focus target images in the fundus image picked up by the image pickup element 38. In addition, the control unit 80 detects corneal astigmatism of the eye E based on the alignment target image picked up by the image pickup element 65. The control unit 80 is connected with the monitor 8 and controls the image displayed on the monitor 8. The control unit 80 is connected with the moving mechanism 49, the moving mechanism 46, the inserting/removing mechanism 39, a switch unit 84 having various switches, a memory 85 as storage means, the light sources, and other constituent elements. The switch unit 84 preferably comprises a focus adjustment switch 84a, a photographing starting switch 84b, a changeover switch 84c for inserting and removing the diopter correction lenses 32a and 32b.

Descriptions of operations of the apparatus having the configuration as described above will be given. First, the examiner makes the face of the examinee supported by a face support unit (not shown). Then, the examiner performs alignment of the apparatus with respect to the eye E by performing tilting operation of a joystick (not shown) in order to laterally and horizontally move the apparatus main body incorporating the optical systems described above in this occasion, the alignment can be smoothly performed by outputting the anterior-segment image picked up by the anterior-segment observation optical system 60 to the monitor 8.

When the rough alignment is completed, the fundus image picked up by the image pickup element 38 is displayed on the monitor 8. While observing the fundus image, the examiner finely adjusts the alignment state by manually operating the joystick in order to allow photographing to be performed in a desired state.

After the fine alignment with the observation of the fundus image, the focus target images S1 and S2 from the projection optical system 40 are displayed in the center as shown in FIG. 2A, and accordingly the focusing lens 32 is moved in the optical axis direction based on the focus target images S1 and S2 in order to perform focusing on the fundus.

Figure 3A:
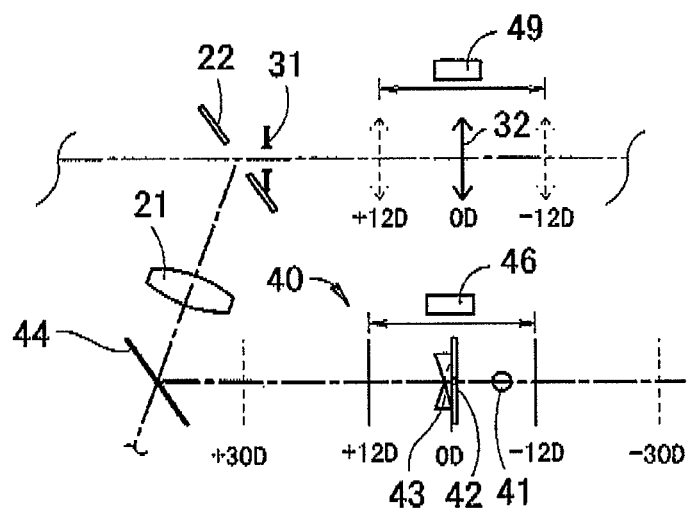
FIGS. 3A to 3C show examples of a movable range of a target projection optical system which is set in accordance with an insertion and removal state of diopter correction lenses.

In the initial state, the diopter correction lenses 32a and 32b are being removed from the photographing optical path, and accordingly the control unit 80 moves the part of the projection optical system 40 in the optical axis direction in conjunction with the movement of the focusing lens 32 within the movable range corresponding to the diopter correction range which is obtained only by the movement of the focusing lens 32 (see FIG. 3A).

The focusing is performed either manually by the examiner using the focus adjustment switch 84a or automatically by the control unit 80. In the case of automatic focusing, the control unit 80 controls driving of the moving mechanism 49 so that the focus target images S1 and S2 coincide. After the focusing is completed, photographing is performed based on a trigger signal for starting photographing which is outputted either automatically or manually.

When the trigger signal for starting photographing is generated, the control unit 80 drives the inserting/removing mechanism 3) to remove the pop-up mirror 34 from the optical path, drives the inserting/removing mechanism 66 to remove the dichroic mirror 24 from the optical path, and controls the photographing light source 14 to emit light. At the same time, the fundus photographing image is picked up by the image pickup element 35, and image data is stored in the memory 85. Then, the control unit 80 controls the monitor 8 to change the image displayed thereon to the fundus photographing image in color picked up by the image pickup element 35.

In the above configuration, if focusing cannot be performed because the eye has severe myopia or severe hyperopia, the examiner presses the changeover switch 84c to insert the diopter correction lens 32a or 32b into the photographing optical path in order to perform focusing. The diopter correction lens 32a or 32b may be automatically inserted. For example, if focusing is not achieved even though the focusing lens 32 is moved to a movement limit position, the diopter correction lens 32a or 32b is automatically inserted.

The control unit 80 controls the moving mechanism 49 to move the part of the projection optical system 40 to a position corresponding to a diopter correction amount which is obtained by the insertion of the diopter correction lens 32a or 32b and the position to which the focusing lens 32 is moved.

To be specific, the position to which the part of the projection optical system 40 including the light source 41 is moved is corrected in accordance with the insertion/removal state of the diopter correction lenses 32a and 32b. For example, the control unit 80 detects the insertion states of the individual diopter correction lenses 32a and 32b into the photographing optical path based on a signal from a sensor which may be placed in the vicinity of the diopter correction lenses 32a and 32b (e.g., a photo sensor), a changeover signal outputted from the changeover switch 84c, a driving signal from the driving unit 32c, or other signals.

Figure 3B:
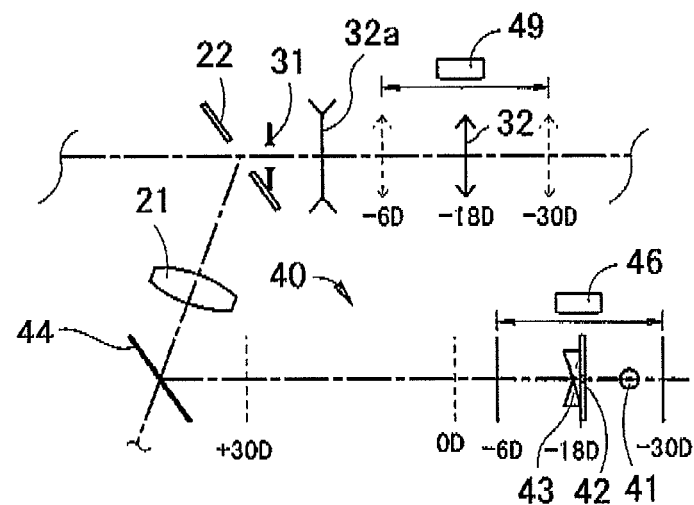
Figure 3C:
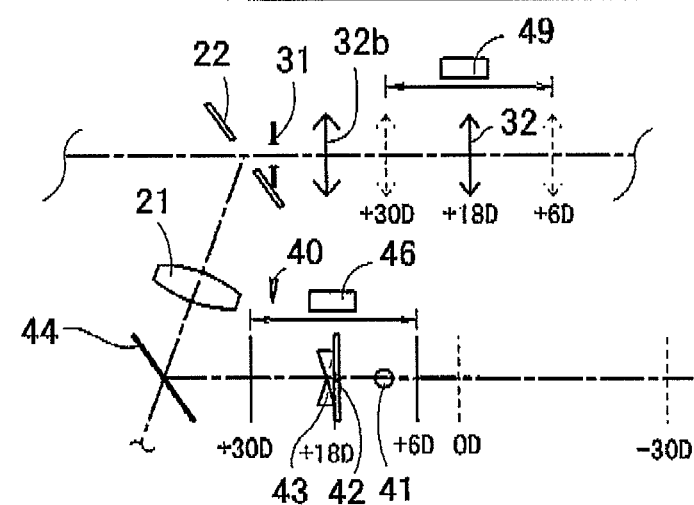

FIGS. 3A to 3C are views showing examples of the movable range of the part of the projection optical system 40 in the state of the diopter correction lenses 32a and 32b being removed, in the state of the diopter correction lens 32a being inserted, and in the state of the diopter correction lens 32b being inserted. In the state of the diopter correction lenses 32a and 32b being removed, the movable range is set corresponding to a given diopter correction range which is obtained by the movement of the focusing lens 32 with the diopter correction lenses 32a and 32b being removed (a range from −12 D to +12 D with 0 D in between).

In the state of the diopter correction lens 32a being inserted as shown in FIG. 3B (e.g., a lens with a diopter correction amount of −18 D being inserted), the movable range is set corresponding to a given diopter correction range which is obtained by the movement of the focusing lens 32 with the diopter correction lens 32a being inserted (a range from −30 D to −6 D with −18 D in between).

To be specific, when the diopter correction lens 32a is inserted, the control unit 80 sets a moving direction (a minus direction) and a moving distance of the part of the projection optical system 40 corresponding to the diopter correction amount of the diopter correction lens 32a (e.g., −18 D). For example, the control unit 80 moves the part of the projection optical system 40 to a position (−30 D) which is the sum of the position to which the part of the projection optical system 40 is moved before the diopter correction lens 32a is inserted (−12 D) and the diopter correction amount of the diopter correction lens 32a (−18 D).

Alternatively, the control unit 80 may control the driving of the moving mechanism 49 to move the focusing lens 32 to a position corresponding to the diopter correction amount before the diopter correction lens 32a is inserted. Thus, focus adjustment from the diopter correction amount in the state of the diopter correction lens 32a being removed can be performed after the diopter correction lens 32a is inserted.

In the state of the diopter correction lens 32b being inserted as shown in FIG. 3C (e.g., a lens with a diopter correction amount of +18 D being inserted), the movable range is set corresponding to a given diopter correction range which is obtained by the movement of the focusing lens 32 with the diopter correction lens 32b being inserted (a range from +6 D to +30 D with −18 D in between). Operations of the control unit 80 may be the same as the operations when the diopter correction lens 32a is being inserted, and detailed descriptions are omitted.

When the movement of the part of the projection optical system 40 is completed as described above, focusing can be performed on an eye with severe ametropia. Accordingly, the control unit 80 controls the driving of the moving mechanism 49 to perform focusing on the fundus based on the separation information of the focus target images S1 and S2 in order that the focus target images S1 and S2 coincide. The examiner may manually perform focusing on the fundus in order that the focus target images S1 and S2 coincide.

The control unit 80 moves the part of the projection optical system 40 in the optical axis direction in conjunction with the movement of the focusing lens 32 within the movable range corresponding to the diopter correction range which is obtained by the insertion of the diopter correction lens and the movement of the focusing lens 32. For example, when the diopter correction lens 32a is inserted, the control unit 80 moves the part of the projection optical system 40 within the movable range corresponding to the diopter correction lens 32a. When the focusing lens 32 is moved, the control unit 80 moves the part of the projection optical system 40 by the diopter correction amount which is obtained by the movement of the focusing lens 32.

Owing to the above configuration, the focus target images on the fundus can be picked up by the image pickup element 38 even if the eye E has severe ametropia and the diopter correction lens is being inserted into the photographing optical path of the photographing optical system 30. Thus, proper automatic focusing control becomes possible. Manual focusing by the examiner also becomes possible by the same operation as that in the state of the diopter correction lenses 32a and 32b being removed.

In the above configuration, another correction lens corresponding to the insertion of the diopter correction lens may be provided so as to be insertable into and removable from the optical path of the projection optical system 40. For example, when the diopter correction lens 32a is inserted, a negative power lens corresponding to the diopter correction amount of the diopter correction lens 32a is inserted between the polarization beam splitter 44 and the prisms 43. This operation saves the movement amount of the part of the projection optical system 40. In this case, the movable range of the part of the projection optical system 40 in the state of the diopter correction lens 32a being inserted and the movable range of the part of the projection optical system 40 in the state of the diopter correction lens 32a being removed can be made substantially equal.

Figures 4A, 4B:
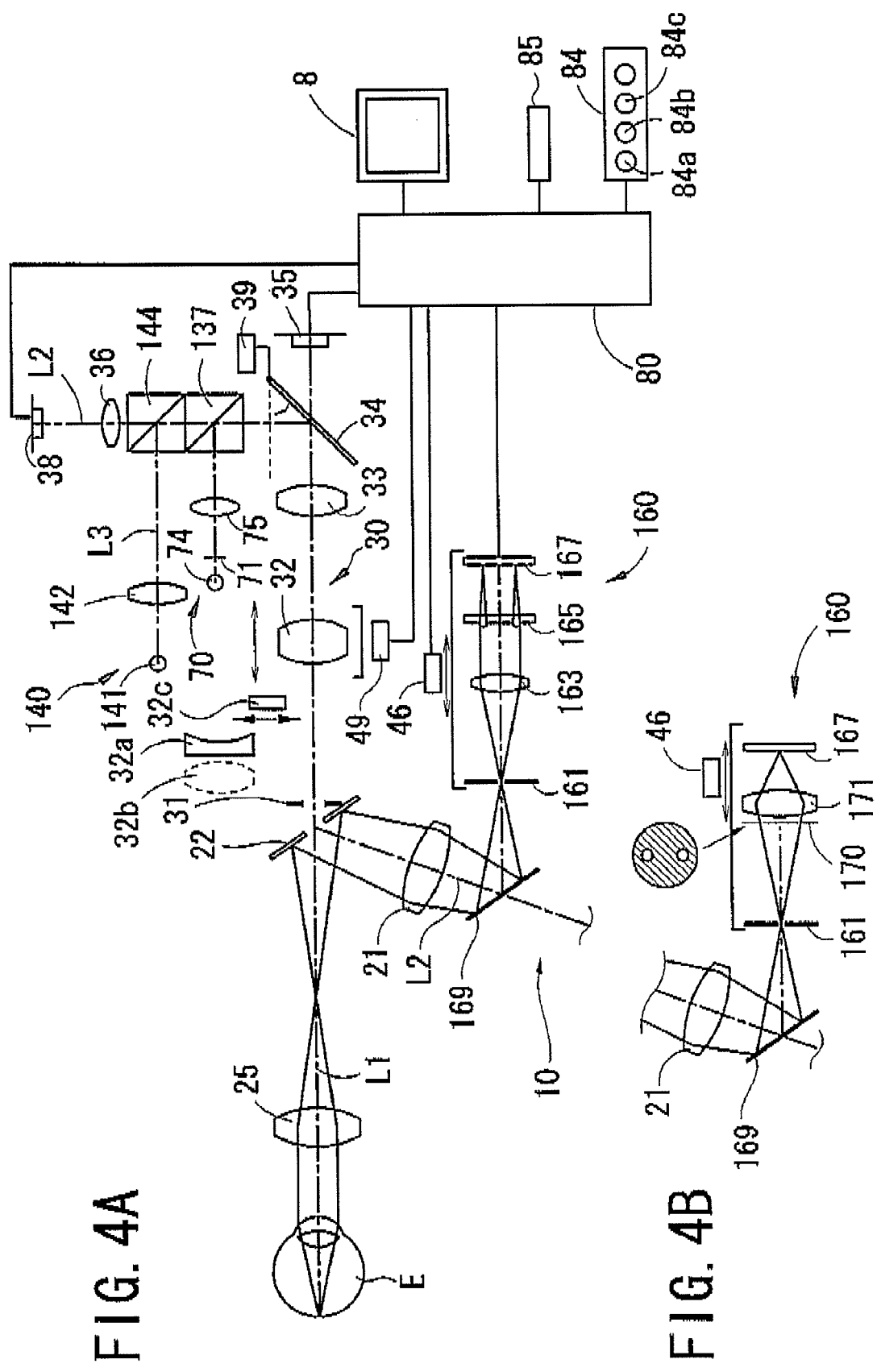
FIGS. 4A and 4B are a schematic view showing an optical system and a control system of a fundus camera according to a second preferred embodiment of the present invention.

Next, a description of a second preferred embodiment of the present invention is provided. The constituent elements in FIGS. 4A and 4B, which are assigned the same reference numerals as the constituent elements in FIG. 1, have the same configurations and functions as the constituent elements in FIG. 1 unless descriptions are particularly provided. In FIGS. 4A and 4B, for detection of the focusing state of the apparatus with respect to the fundus, a target projection optical system 140 for projecting spot light onto the fundus via a center of the pupil and a photo-receiving optical system 160 for picking up the light reflected from the fundus via the anterior-segment as a given pattern image (e.g., a ring pattern image, a plurality of spot images) and making the image photo-received on a two-dimensional photodetector.

As shown in FIG. 4A, the projection optical system 140 comprises an infrared point light source 141 such as an LED and an SLD, a projection lens 142, and a beam splitter 144 which functions as an optical path dividing member for dividing the focus light and the fundus observation light (e.g., a dichroic mirror which performs wavelength separation on the focus light and the fundus observation light), which are placed on an optical axis L3. The projection optical system 140 shares the optical path from the beam splitter 144 through the objective lens 25 with the fundus observation optical system 30. A dichroic mirror 137 has properties of reflecting visible light and transmitting infrared light.

The photo-receiving optical system 160 comprises a beam splitter 169, a pinhole plate 161 with an opening which is placed at a position substantially conjugate with the fundus, a collimator lens 163, a ring lens 165, and a two-dimensional photodetector 167 which is placed at a position substantially conjugate with the fundus, which are placed in a reflecting direction of the beam splitter 169. The photo-receiving optical system 160 shares the optical path from the objective lens 25 through the beam splitter 169 with the illumination optical system 10. A part of the photo-receiving optical system 160 including the two-dimensional photodetector 167 (e.g., the pinhole plate 161 through the two-dimensional photodetector 167) is movable in the direction of an optical axis in conjunction with the movement of the focusing lens 32 by the driving of the moving mechanism 46. For example, when the focusing lens 32 is located in a position for an emmetropic eye, the part of the photo-receiving optical system 160 including the two-dimensional photodetector 167 is moved so that the fundus of the emmetropic eye and the opening of the pinhole plate 161 are substantially conjugate. When the focusing lens 32 is located in a position such that focusing is achieved on an eye with given sphere power (e.g., −3 D), the part of the photo-receiving optical system 160 including the two-dimensional photodetector 167 is moved so that the fundus and the opening of the pinhole plate 161 are substantially conjugate. A position to which the part of the photo-receiving optical system 160 including the two-dimensional photodetector 167 is moved in conjunction with the movement of the focusing lens 32 is corrected in accordance with the insertion/removal state of the diopter correction lenses 32a and 32b as in the case of moving the part of the projection optical system 40 including the light source 41 according to the first preferred embodiment of the present invention in FIG. 1.

The ring lens 165 comprises a lens portion and a ring target plate having a ring opening, and is placed at a position substantially conjugate with the pupil. The two-dimensional photodetector 167 is placed at a focal point of the ring portion, and becomes conjugate with the fundus when focusing is achieved between the fundus and the image pickup element 38 (the image pickup element 35). The ring target plate is placed between the focusing lens 32 and the two-dimensional photodetector 167 in a position substantially conjugate with the anterior-segment (e.g. a position substantially conjugate with the pupil, a position substantially conjugate with the fundus).

Light emitted from the light source 141 passes through the lens 142 through the objective lens 25 via the pop-up mirror 34 to be projected onto the fundus, so that a spot-shaped point light source image is projected onto the fundus. The point light source image is reflected and scattered by the fundus to exit from the eye E, passes through the objective lens 25, is reflected by a reflection plane of the apertured mirror 22, passes through the relay lens 21, the beam splitter 169, the opening of the pinhole plate 161, the collimator lens 163, is converged by the ring lens 165, and is photo-received on the two-dimensional photodetector 167 as a ring image.

A photo-receiving signal from the two-dimensional photodetector 167 is inputted to the control unit 80. When the fundus is in focus, a thin ring image with less blur having the same size as the ring opening of the ring lens 165 is photo-received on the two-dimensional photodetector 167. When the fundus is out of focus, a thick ring image with blur having a size different from the ring image which is obtained when the fundus is in focus is photo-received on the two-dimensional photodetector 167. If the eye has spherical ametropia, the ring image has a size in proportion to the degree of the spherical ametropia. If the eye has astigmatic ametropia, the ring image photo-received on the two-dimensional photodetector 167 has an oval shape in accordance with the astigmatic ametropia.

Accordingly, the control unit 80 detects the focusing state of the apparatus with respect to the fundus by analyzing the ring image photo-received on the two-dimensional photodetector 167. The control unit 80 performs focusing on the fundus by controlling the driving of the moving mechanism 46 and the driving of the moving mechanism 49 based on the detected focusing state of the apparatus with respect to the fundus. To be specific, the control unit 80 moves the focusing lens 32 in the optical axis direction by means of the moving mechanism 49 and moves the part of the photo-receiving optical system 160 by means of the moving mechanism 46. For example, the two-dimensional photodetector 167 is brought into a position conjugate with the fundus such that the ring image on the two-dimensional photodetector 167 is made thinnest or brightest. Thus, focus adjustment between the image pickup element 35 (or the image pickup element 38) and the fundus is performed.

In the second preferred embodiment of the present invention, polarization beam splitters having properties of reflecting one light and transmitting the other light, the light having polarizing directions intersecting at right angles, which is used in the first preferred embodiment of the present invention may be used instead of the beam splitter 144 and the beam splitter 169.

In the above configuration, if the astigmatic detection and the ring image obtainment are not performed, a diaphragm 170 with two holes which functions as a pattern target plate in which the two holes are placed at positions whose distances from a photo-receiving optical axis are equal, and an image forming lens 171 functioning as a light collecting member which collects light having passed through the diaphragm 170 on the two-dimensional photodetector 167 may be used as shown in FIG. 4B. In this case, when the fundus is in focus, two spot images coincide so that one spot image on the photo-receiving optical axis is photo-received on the two-dimensional photodetector 167. When the fundus is out of focus, two spot images are photo-received on the two-dimensional photodetector 167.

Because the focus detection optical system is configured such that the focusing state of the apparatus with respect to the fundus is detected by the ring image photo-received on the two-dimensional photodetector 167 (see FIG. 4A), the cause of blur in the image can be judged. The ring image photo-received on the two-dimensional photodetector 167 in the case of the eye with astigmatism has an oval shape with a long diameter and a short diameter. The long diameter and the short diameter of the ring image change depending on astigmatic power of the eye.

The control unit 80 detects the focusing state of the apparatus with respect to the fundus based on the ring image photo-received on the two-dimensional photodetector 167. Then, the control unit 80 controls the driving of the moving mechanism 49 in order that the focusing lens 32 may be located in a position corresponding to spherical equivalent power of the eye based on the detected focusing state of the apparatus with respect to the fundus. In addition, the control unit 80 moves the part of the photo-receiving optical system 160 in conjunction with the movement of the focusing lens 32 (subsequent operations are performed as described above). In the second preferred embodiment of the present invention, the position corresponding to the spherical equivalent power of the eye is set as a focusing completion position.

Here, the control unit 80 detects the position of the ring image in meridian directions and calculates eye refractive power (S: sphere power, C: astigmatic power; A: an astigmatic axial angle) of the eye based on information on the detected position of the ring image. Based on the S value and the C value, the control unit 80 calculates the spherical equivalent power (SE=S+½C; hereinafter, referred to as an SE value).

The control unit 80 controls the monitor 8 to display the ring target image, which is photo-received on the two-dimensional photodetector 167 when the focusing lens 32 is located in the focusing completion position, and the fundus observation image while superimposing the images one another. The control unit 80 may detect information on the position of the obtained ring image and control the monitor 8 to display electronic graphics according to the detected information. The control unit 80 may control the monitor 8 to fixedly display a ring mark based on the ring image which is obtained when the focusing lens 32 is located in the focusing completion position.

After the fundus image is obtained as described above, the control unit 80 controls the monitor 8 to display the ring image, which is obtained at the time when focusing is completed, in association with the obtained fundus image in color.

Figure 5A:
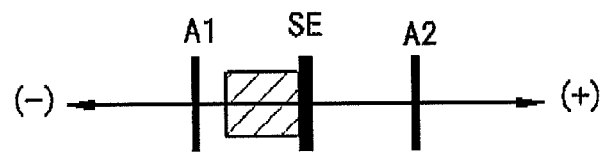
FIGS. 5A and 5B are views in which a focus deviation amount and a focus deviation direction are electronically displayed on a monitor.
Figure 5B:
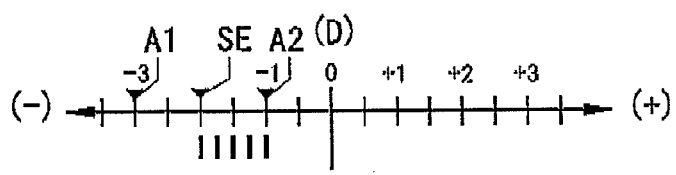

With the focusing lens 32 being located in the position corresponding to the SE value, the control unit 80 detects the focusing state of the apparatus with respect to the fundus with reference to the position to which the focusing lens 32 being located in the position corresponding to the SE value is moved, and controls the monitor 8 to electronically display a focus deviation amount and a focus deviation direction of the apparatus with respect to the fundus (see FIGS. 5A and 5B). In this case, the control unit 80 detects a movement amount of the focusing lens 32 from the position corresponding to the SE value and controls the monitor 8 to electronically display the focus deviation amount and the focus deviation direction.

In FIG. 5A, an indicator is moved in the positive direction or the negative direction with reference to the SE value in accordance with the movement amount of the focusing lens 32 from the position corresponding to the SE value. In FIG. 5B, the position of the focusing lens 32 is converted into refractive power of the eye, and the SE value is indicated by a gauge presenting eye refractive power values in order to display the movement amount of the focusing lens 32 from the position corresponding to the SE value.

The control unit 80 may set a focus position corresponding to refractive power in a steepest meridian direction of astigmatism of the eye as a first focusing limit position, set a focus position corresponding to refractive power in a flattest meridian direction of astigmatism of the eye as a second focusing limit position, and control the monitor 8 to display limit marks corresponding to the first and second focusing limit positions (see FIGS. 5A and 5B). In FIGS. 5A and 5B, graphic marks A1 correspond to the first focusing limit position and graphic marks A2 correspond to the second focusing limit position.

Figure 6:
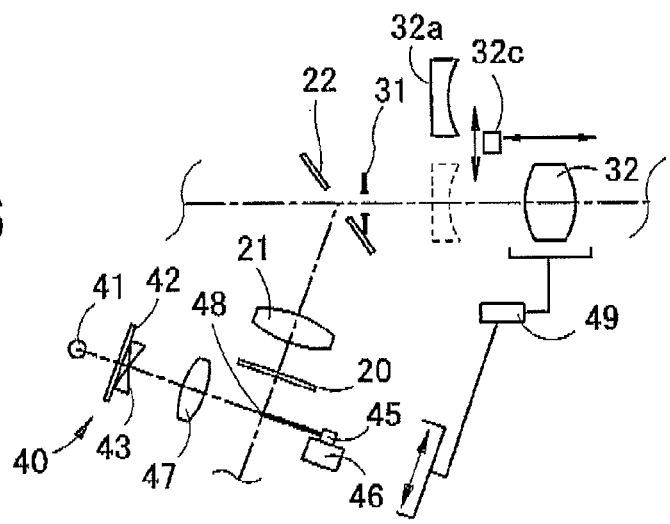
FIG. 6 is a schematic view showing an optical system for illustrating a second focusing mode.

Next, descriptions of a first focusing mode and a second focusing mode are provided. FIG. 6 is a schematic view showing an optical system for illustrating the second focusing mode. As shown in FIG. 6, the projection optical system 40 comprises the infrared light source 41, the slit target plate 42, the two deflection-angle prisms 43 attached to the slit target plate 42, the projection lens 47, and a spot mirror 48 which is placed obliquely on the optical path of the illumination optical system 10. The spot mirror 48 is fixed to the top end of a lever 45, and is normally placed obliquely on the optical path and is removed from the optical path by rotating a rotary solenoid 46 about the shaft with predetermined timing before the photographing. The spot mirror 48 is placed at a position substantially conjugate with the fundus. The light source 41, the slit target plate 42, the deflection-angle prisms 43, the projection lens 47, the spot mirror 48, and the lever 45 are moved in conjunction with the focusing lens 32 in the direction of an optical axis by the moving mechanism 49. The light having passed through the slit target plate 42 is transmitted through the deflection-angle prisms 43 and the projection lens 47, and is reflected by the spot mirror 48, and thereafter the light passes through the relay lens 21, the apertured mirror 22, the dichroic mirror 24, and the objected lens 25, and is projected onto the fundus. When the fundus is out of focus, target images of the slit target plate 42 are separate, and when the fundus is in focus, the target images coincide. The target images projected onto the fundus are picked up by the image pickup element 38 together with the fundus observation image. The other constituent elements in FIG. 6 may have the same configurations as the corresponding constituent elements in FIG. 1, and descriptions thereof are omitted.

Figure 7:
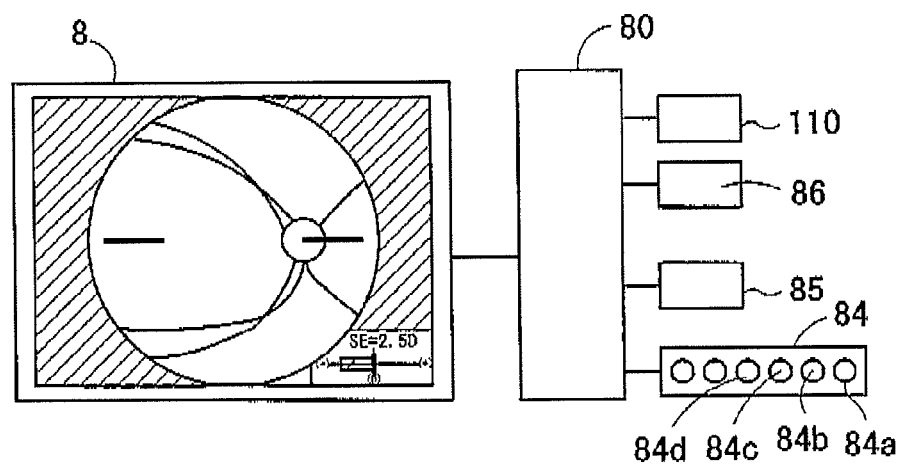
FIG. 7 is a view showing a control system of the apparatus for illustrating the second focusing mode.

FIG. 7 is a view showing a control system of the apparatus or illustrating the second focusing mode. As shown in FIG. 7, the switch unit 84 comprises a mode selection switch 84d for switching between a first focusing mode and the second focusing mode. The constituent elements assigned the same reference numerals as the constituent elements in FIG. 1 have the same configurations and functions as the constituent elements in FIG. 1 unless descriptions are particularly provided.

The control unit 80 is connected with an eye determining unit 110 for determining whether the eye is a right eye or a left eye, and the control unit 80 determines whether the eye is a right eye or a left eye based on an output signal from the eye determining unit 110.

By the use of the mode selection switch 84d, selective switching can be performed between the first focusing mode in which the position to which the focusing lens 32 is moved under automatic focusing control is set as the focusing completion position and the second focusing mode in which the position to which the focusing lens 32 is moved by the driving of the moving mechanism 49 is set based on measurement data obtained by an eye refractive power measurement apparatus.

Also in the second focusing mode, the control unit 80 can control the monitor 8 to display the focusing state of the apparatus with respect to the fundus which is obtained based on a result of the detection by the focus detection optical system as first focusing information (see FIGS. 2A and 2B). Examples of the first focusing information include the split target images which are displayed on the monitor 8 based on the image-pickup signal outputted from the image pickup element 38.

When the second focusing mode is set, the control unit 80 moves the focusing lens 32 based on the measurement data obtained by the eye refractive power measurement apparatus. The control unit 80 sets the focusing completion position of the focusing lens 32 to the position corresponding to the SE value and controls the monitor 8 to display focusing information based on the set position as a second focusing information which is different from the first focusing information.

The control unit 80 moves the focusing lens 32 based on the measurement data corresponding to a result of the eye determination by the eye determining unit 110. Here, the control unit 80 corrects astigmatism of the eye by controlling the driving of the moving mechanism 49 to automatically move the focusing lens 32 to the position corresponding to the SE value which is calculated based on the sphere power and the astigmatic power of the eye in the measurement data.

Figure 8A:
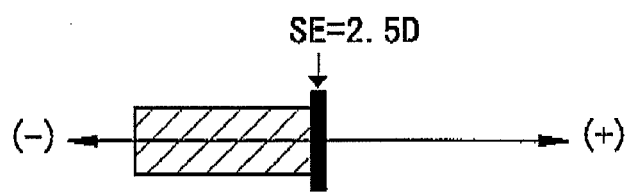
FIGS. 8A and 8B are enlarged views of second focusing information.
Figure 8B:
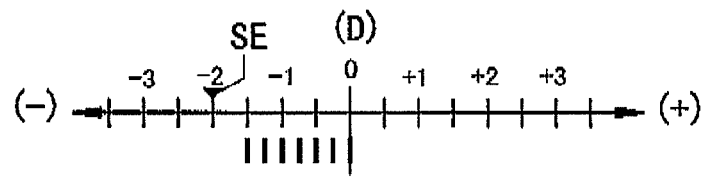

FIG. 7 is a view in which the second focusing information is displayed together with the fundus observation image. FIGS. 8A and 8B are enlarged views of the second focusing information. When the focusing lens 32 is moved to the position corresponding to the SE value, the control unit 80 detects the focusing state of the apparatus with respect to the fundus with reference to the position of the focusing lens 32 corresponding to the SE value and controls the monitor 8 to display a focus deviation amount and a focus deviation direction of the apparatus with respect to the fundus which are obtained based on a result of the detection as the second focusing information. The control unit 80 controls the monitor 8 not to display the first focusing information when the second focusing information is displayed.

In FIG. 8A, an indicator is moved in the positive direction or the negative direction with reference to the SE value in accordance with the movement amount of the focusing lens 32 from the position corresponding to the SE value. In FIG. 8B, the position of the focusing lens 32 is converted into refractive power of the eye, and a mark for the SE value is provided in a gauge presenting eye refractive power values in order to display the movement amount of the focusing lens 32 from the position corresponding to the SE value.

Thus, the examiner is allowed to perform focusing on a desired portion while checking the focus deviation amount and the focus deviation direction from the position corresponding to the SE value based on the focus target images which are electronically displayed on the monitor 8 (see FIGS. 8A and 8B). Limit marks similar to the limit marks in FIGS. 5A and 5B may be displayed.

Figure 9A:
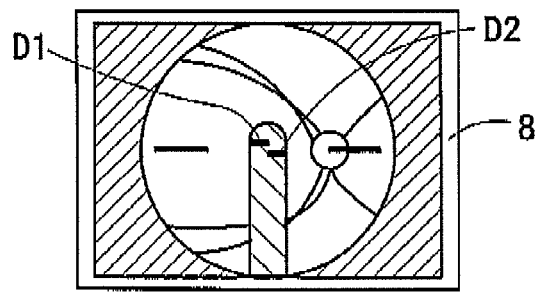
FIGS. 9A and 9B are views in which electronic graphics depicting two focus bars are displayed as first focusing information or second focusing information.
Figure 9B:
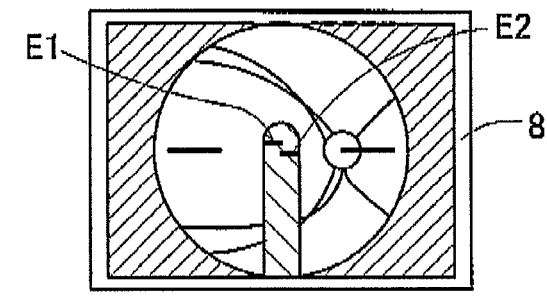
Figure 10A:
FIGS. 10A and 10B are views in which a display pattern of the focus bars are changed between the first focusing information and the second focusing information.
Figure 10B:
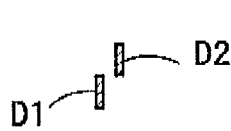

Electronic graphics (see marks D1 and D2 in FIG. 9A) which are displayed as the second focusing information may depict the focus bars (focus target images) which are displayed as the first focusing information. In addition, the first focusing information may be electronically displayed (see marks E1 and E2 in FIG. 9B). FIGS. 10A and 10B are views in which a display pattern of the focus bars is changed between the first focusing information and the second focusing information.

Next, a description of a technique for determining whether or not corneal astigmatism is present in the eye based on image forming positions on the two-dimensional photodetector at which images of targets projected onto the cornea are formed is given referring to FIG. 6. The other constituent elements may be the same as the corresponding constituent elements in FIG. 1, and they are omitted from the illustration in FIG. 6. The alignment target projection optical system 50 doubles as a corneal target projection optical system for projecting targets for corneal astigmatism detection onto the cornea. The anterior-segment observation optical system 60 doubles as a target detection optical system for detecting the targets projected onto the cornea.

Figure 11:
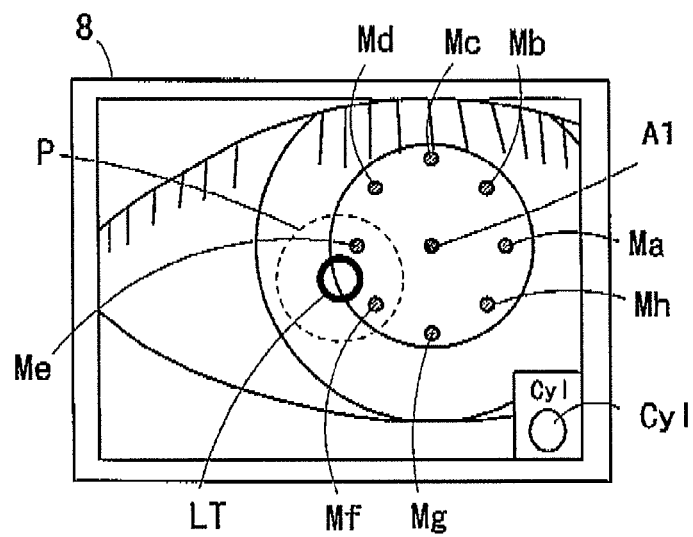
FIG. 11 is a view showing an observation screen for an anterior-segment image picked up by an image pickup element.
Figure 12A:
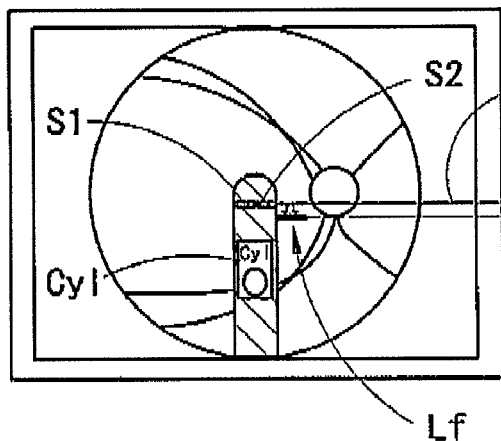
FIGS. 12A and 12B are view showing a fundus observation screen.
Figure 12B:
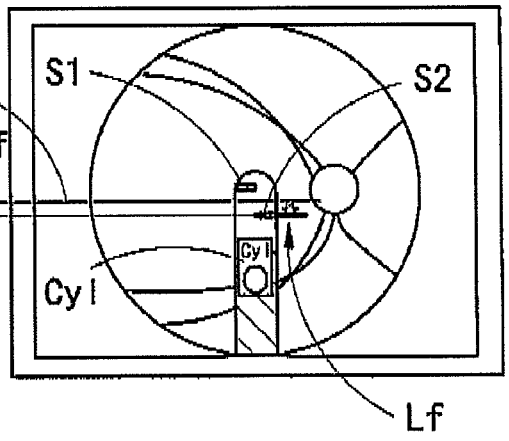

FIG. 11 is a view showing an observation screen for the anterior-segment image picked up by the image pickup element 65. FIGS. 12A and 12B are views showing a fundus observation screen. The control unit 80 determines whether or not corneal astigmatism is present in the eye based on image forming positions of corneal target images Ma to Mh on the image pickup element 65, and controls the monitor 8 to display a result of the determination together with the fundus photographing image (or the fundus observation image or the anterior-segment image). In addition, the control unit 80 controls the monitor 8 to make a guiding instruction to move the focusing lens 32 to a position corresponding to an average value of corneal refractive power of the eye based on the image forming positions of the target images Ma to Mh on the image pickup element 65.

Figure 13:
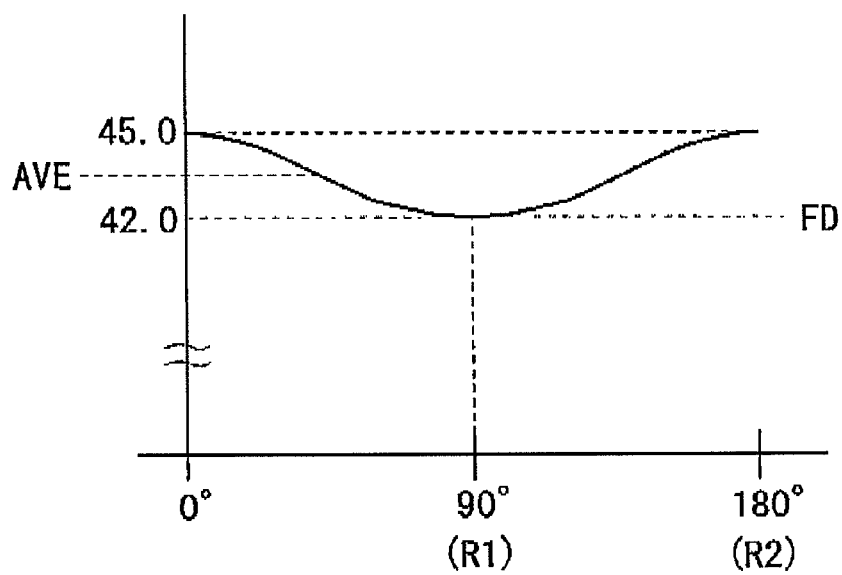
FIG. 13 is a graph showing an example of corneal refractive power in meridian directions as a result of corneal refractive power calculation.

To be more specific, the control unit 80 calculates corneal curvature of the cornea Ec by detecting the heights of the target images Ma to Mh. FIG. 13 is a graph showing an example of corneal refractive power in meridian directions as a result of the calculation. The graph in FIG. 13 shows that corneal refractive power in the flattest meridian (R1) direction is 42.0 D, corneal, refractive power in the steepest meridian (R2) direction is 45.0 D, corneal astigmatic power CYL is −3.0 D (taking the negative side), and a corneal astigmatic axial angle A is 90 degrees.

When the corneal refractive power is calculated as described above, the control unit 80 determines whether or not corneal astigmatism is present in the eye based on whether an absolute value of the calculated corneal astigmatic power CYL is beyond a predetermined value (e.g. 0.5 D). When it is determined that the corneal astigmatism is present in the eye, the control unit 80 controls the monitor 8 to inform that the eye has astigmatism (see icons Cyl in FIGS. 11, 12A, and 12B).

Descriptions of operations of the control unit 80 when it is determined that the corneal astigmatism is present in the eye are provided below. When it is determined that corneal astigmatism is present in the eye, the control unit 80 controls the monitor 8 to display a result of the determination (see the icons Cyl in FIGS. 12A and 12B) together with the fundus observation image. In addition, the control unit 80 controls the monitor 8 to make a guiding instruction to move the focusing lens 32 to the position corresponding to the average value of the corneal refractive power.

To be specific, the control unit 80 calculates the average value of the refractive power in the R1 direction and the refractive power in the R2 direction (average refractive power AVE) based on the calculated refractive power data. In addition, the control unit 80 calculates corneal refractive power FD in the direction of separation between the target image images S1 and S2 (a vertical direction). In the case of the data shown in FIG. 13, average refractive power AVE of 43.5 D ((42.0+45.0)/2) and corneal refractive power FD of 42.0 are obtained.

Next, the control unit 80 detects a deviation of the corneal refractive power FD from the average refractive power AVE as a deviation amount H (H=AVE−FD). Then, the control unit 80 calculates a direction in which the focusing lens 32 is to be moved and a moving amount of the focusing lens 32 with respect to the coinciding position of the focus target images S1 and S2 based on the deviation degree and the deviation direction, and controls the monitor 8 to make a guiding instruction indicating the obtained moving direction and the obtained moving amount. The deviation amount H defines the deviation direction and the deviation amount (the deviation degree) between the position corresponding to the average refractive power AVE to which the focusing lens 32 is moved and the position to which the focusing lens 32 is moved when the focus target images S1 and S2 coincide. The deviation direction is defined by negative and positive values of the deviation amount H, and the deviation amount is defined by an absolute value of the deviation amount H.

For displaying the guiding instruction, the monitor 8 may electronically display a retile mark Lf indicating a direction in which the focus target images S1 and S2 are to be moved (an operating direction of a focus knob) and a moving amount of the focus target images S1 and S2 (an operation amount of the focus knob) based on the deviation amount H calculated as described above. The control unit 80 changes a deviation amount ΔLf of the display position of the reticle mark Lf with respect to a reference display position K (the target coinciding position) in accordance with the degree of the absolute value of the deviation amount H.

When the focus knob is operated by the examiner so that the display positions in the vertical direction of the reticle mark Lf and the focus target image S2 coincide, the focusing lens 32 is located in the position corresponding to the average corneal refractive power AVE.

After the photographing, the fundus image picked up by the image pickup element 35 is stored in the memory 85. The control unit 80 controls the monitor 8 to display the result of the determination that the corneal astigmatism is present in the eye (see the icons Cyl in FIGS. 12A and 12B) together with the fundus photographing image.

Considering a fact that corneal astigmatism constitutes most of astigmatism, the above configuration allows diopter correction to be performed on a number of astigmatic eyes. In the above preferred embodiments of the present invention, taking advantage that the detected positions of the target images on the cornea and the corneal curvature (corneal refractive power) of the eye have a given correspondence relation, the determination whether or not corneal astigmatism is present in the eye and the guiding instruction to move the focusing lens based on the detected positions of the target images may be performed without calculating the corneal refractive power. If the target projection optical system is configured to project at least three point light sources onto the cornea Ec, corneal curvature measurement with astigmatism detection can be performed.

Figure 14:
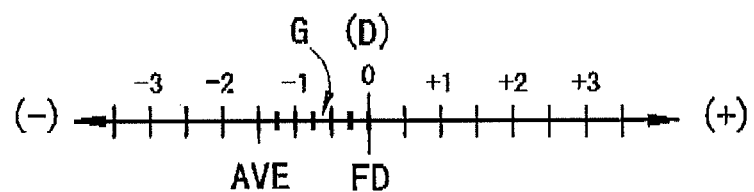
FIG. 14 is a view showing an example of displaying focusing information.

Indicators as shown in FIG. 14 may be displayed when the above electronic display is performed. In addition, the driving of the moving mechanism 49 may be controlled. To be specific, the control unit 80 detects the deviation of the corneal refractive power FD from the average corneal refractive power AVE (the deviation amount H), and calculates the moving direction and the moving amount of the focusing lens 32 with respect to the coinciding position of the focus target images S1 and S2 based on the deviation direction and the deviation degree. The control unit 80 controls the driving of the moving mechanism 49 based on the obtained moving direction and the obtained moving amount.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an examinee's eye, the fundus camera comprising:
   an illumination optical system comprising an illumination light source and arranged to illuminate the fundus with illumination light emitted from the illumination light source via an objective lens;
   a photographing optical system comprising a focusing lens movable in an optical axis direction thereof, arranged to photograph the fundus by photo-receiving the illumination light reflected from the fundus via the objective lens and the focusing lens, and comprising a diopter correction lens arranged to correct a diopter of severe ametropia and to be additionally inserted into an optical path of the photographing optical system;
   a focus detection optical system comprising
      a projection optical system comprising a projection light source and a first polarizing member, arranged to project focus target light in a first polarizing direction onto the fundus without using a black dot plate arranged to remove reflection from the objective lens, and
      a photo-receiving optical system comprising a photodetector and a second polarizing member arranged to make focus target light in a second polarizing direction orthogonal to the first polarizing direction enter the photodetector, arranged to photo-receive the focus target light in the second polarizing direction that is reflected from the fundus, and shared by an observation optical system arranged to observe the fundus;
   eye refractive power measurement data obtaining means arranged to obtain measurement data including astigmatic power of the eye; and
   moving means arranged to move the focusing lens, the diopter correction lens, and a part of the projection optical system based on data of the focus detection optical system and the data of the eye refractive power measurement data obtaining means so as to set a focus position of the photographing optical system at a position corresponding to spherical equivalent power of the eye.

2. A fundus camera for photographing a fundus of an examinee's eye, the fundus camera comprising:
   an illumination optical system comprising an illumination light source and arranged to illuminate the fundus with illumination light emitted from the illumination light source via an objective lens;
   a fundus photographing optical system comprising a focusing lens movable in an optical axis direction thereof, and arranged to photograph the fundus by photo-receiving the illumination light reflected from the fundus via the objective lens and the focusing lens;
   eye refractive power measurement data obtaining means arranged to obtain measurement data including astigmatic power of the eye;
   a focus detection optical system comprising
      a projection optical system comprising a projection light source and arranged to project focus target light onto the fundus, and
      a photo-receiving optical system comprising a photodetector and arranged to photo-receive the focus target light reflected from the fundus;
   a monitor; and
   a control means arranged to control the monitor to display focusing information,
   wherein the control means is arranged to set focusing information from the focus detection optical system as first focusing information, obtain spherical equivalent power of the eye based on the measurement data obtained by the eye refractive power measurement data obtaining means, set focusing information with reference to the spherical equivalent power of the eye as second focusing information, and control the monitor to switch display between the first focusing information and the second focusing information.

3. A fundus camera for photographing a fundus of an examinee's eye, the fundus camera comprising:
   an illumination optical system comprising an illumination light source and arranged to illuminate the fundus with illumination light emitted from the illumination light source via an objective lens;
   a photographing optical system comprising a focusing lens movable in an optical axis direction thereof and arranged to photograph the fundus by photo-receiving the illumination light reflected from the fundus via the objective lens and the focusing lens;
   a focus detection optical system comprising
      a projection optical system comprising a projection light source and arranged to project focus target light onto the fundus, and
      a photo-receiving optical system comprising a photodetector and arranged to photo-receive the focus target light reflected from the fundus;
   eye refractive power measurement data obtaining means arranged to obtain measurement data including astigmatic power of the eye;
   a monitor; and
   control means arranged to determine whether or not the astigmatic power is beyond a predetermined value and control the monitor to display a result of the determination.

4. A fundus camera for photographing a fundus of an examinee's eye, the fundus camera comprising:
   an illumination optical system comprising an illumination light source and arranged to illuminate the fundus with illumination light emitted from the illumination light source via an objective lens;
   a photographing optical system comprising a focusing lens movable in an optical axis direction thereof, arranged to photograph the fundus by photo-receiving the illumination light reflected from the fundus via the objective lens and the focusing lens, and comprising a diopter correction lens arranged to correct a diopter of severe ametropia and to be additionally inserted into an optical path of the photographing optical system;
   a focus detection optical system comprising
      a projection optical system comprising a projection light source and a first polarizing member, arranged to project focus target light in a first polarizing direction onto the fundus without using a black dot plate arranged to remove reflection from the objective lens, and a photo-receiving optical system comprising a photodetector and a second polarizing member arranged to make focus target light in a second polarizing direction orthogonal to the first polarizing direction enter the photodetector, arranged to photo-receive the focus target light in the second polarizing direction that is reflected from the fundus, and shared by an observation optical system of the fundus; and moving means arranged to move the focusing lens, the diopter correction lens, and a part of the projection optical system based on data of the focus detection optical system so as to perform focusing of the photographing optical system.

* * * * *